United States Patent [19]
Drazen et al.

[11] Patent Number: 6,156,503
[45] Date of Patent: Dec. 5, 2000

[54] DIAGNOSING ASTHMA PATIENTS PREDISPOSED TO ADVERSE β-AGONIST REACTIONS

[75] Inventors: Jeffrey M. Drazen, Winchester, Mass.; Vern Chinchilli, Elizabethtown, Pa.; Richard Martin, Englewood, Colo.; Robert Lemanske, Madison, Miss.; Jean G. Ford, Newark, N.J.; James E. Fish, Gladwyne, Pa.; Homer Boushey, San Francisco, Calif.

[73] Assignees: The Regents of the University of California, Oakland, Calif.; The Trustees of Columbia University in the City of New York, New York, N.Y.; The Penn State Research Foundation, University Park, Pa.; National Jewish Medical and Research Center, Denver, Colo.; Wisconsin Alumni Research Center, Madison, Wis.; Thomas Jefferson University, Philadelphia, Pa.; Brigham and Women's Hospital, Boston, Mass.

[21] Appl. No.: 08/811,441

[22] Filed: Mar. 3, 1997

[51] Int. Cl.[7] .............................. C12Q 1/68; C07H 21/04
[52] U.S. Cl. .......................... 435/6; 435/91.2; 536/23.5; 536/24.31; 536/24.33
[58] Field of Search ..................... 435/6, 91.2; 536/23.5, 536/24.31, 24.33; 935/8, 9, 78

[56] References Cited

FOREIGN PATENT DOCUMENTS

WO 96/25517  8/1996  WIPO.

OTHER PUBLICATIONS

Reihsaus et al. American J. Resp. Cell Molec. Biol. 83:334–339, 1993.
Green et al. Biochemistry. 33: 9414–9419, 1994.
Martinez et al. Journal of Clinical Investigation. 100: 3184–3188, 1997.
Hancox, et al., "Polymorphism of the $\beta_2$–Adrenoceptor and the Response to Long–Term $B_2$–Agonist Therapy in Asthma," Eur. Respir. J., vol. 11, pp. 589–593, 1998, (month unavailable).
Sears et al., "Regular inhaled beta–agonist treatment in bronchial asthma", The Lancet, vol. 336, pp. 1391–1396, Dec. 8, 1990.
Drazen et al., "Comparison of Regularly Scheduled with As–Needed Use of Albuterol in Mild Asthma" NE J. Med. 335(12):841–7, Sep. 1, 1996.
Green et al., "Influence of beta–2 adrenergic receptor genotypes on signal transduction in human airway smooth muscle cells" Amer. J. Respir. Cell Molec. Bio.13(1):25–33, Jul. 1995.
Green et al., "Implications of genetic variability of human beta–2 adrenergic structure" Pulmon. Pharm. 8(1):1–10, Feb. 1995.
Kamada et al., "Issues in the Use of Inhaled Glucocorticoids" Americ. J Respir. Crit. Care Med. 153(6 pt 1):1739–48, Jun. 1996.

Primary Examiner—Carla J. Myers
Attorney, Agent, or Firm—Choate, Hall & Stewart

[57] ABSTRACT

The present invention provides a novel method for identifying individuals who are likely to have negative responses to regular administration of β-agonists. The invention also provides kits useful for this purpose.

10 Claims, 3 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
    (A) LENGTH: 413 amino acids
    (B) TYPE: amino acid
    (C) STRANDEDNESS: Not Relevant
    (D) TOPOLOGY: Not Relevant   (ii) MOLECULE TYPE: protein   (vii) IMMEDIATE SOURCE:
    (B) CLONE: Human Beta-2-Adrenergic Receptor Protein   (xi) SEQUENCE DESCRIPTION: SEQ ID NO:1:

```
Met Gly Gln Pro Gly Asn Gly Ser Ala Phe Leu Leu Ala Pro Asn Arg
  1               5                  10                  15

Ser His Ala Pro Asp His Asp Val Thr Gln Gln Arg Asp Glu Val Trp
             20                  25                  30

Val Val Gly Met Gly Ile Val Met Ser Leu Ile Val Leu Ala Ile Val
         35                  40                  45

Phe Gly Asn Val Leu Val Ile Thr Ala Ile Ala Lys Phe Glu Arg Leu
 50                  55                  60

Gln Thr Val Thr Asn Tyr Phe Ile Thr Ser Leu Ala Cys Ala Asp Leu
 65                  70                  75                  80

Val Met Gly Leu Ala Val Val Pro Phe Gly Ala Ala His Ile Leu Met
             85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
            115                 120                 125

Val Asp Arg Tyr Phe Ala Ile Thr Ser Pro Phe Lys Tyr Gln Ser Leu
        130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300
```

```
         Lys Glu Val Tyr Ile Leu Leu Asn Trp Ile Gly Tyr Val Asn Ser Gly
         305                 310                 315                 320

Phe Asn Pro Leu Ile Tyr Cys Arg Ser Pro Asp Phe Arg Ile Ala Phe
                         325                 330                 335

Gln Glu Leu Leu Cys Leu Arg Arg Ser Ser Leu Lys Ala Tyr Gly Asn
                     340                 345                 350

Gly Tyr Ser Ser Asn Gly Asn Thr Gly Glu Gln Ser Gly Tyr His Val
                     355                 360                 365

Glu Gln Glu Lys Glu Asn Lys Leu Leu Cys Glu Asp Leu Pro Gly Thr
                 370                 375                 380

Glu Asp Phe Val Gly His Gln Gly Thr Val Pro Ser Asp Asn Ile Asp
         385                 390                 395                 400

Ser Gln Gly Arg Asn Cys Ser Thr Asn Asp Ser Leu Leu
                         405                 410

(2) INFORMATION FOR SEQ ID NO:2:

(i) SEQUENCE CHARACTERISTICS:
        (A) LENGTH: 3451 base pairs
        (B) TYPE: nucleic acid
        (C) STRANDEDNESS: both
        (D) TOPOLOGY: Not Relevant (ii) MOLECULE TYPE: cDNA (vii) IMMEDIATE SOURCE:
        (B) CLONE: HUman Beta-2-Adrenergic Receptor Gene (xi) SEQUENCE DESCRIPTION: SEQ ID NO:2:

CCCGGGTTCA AGAGATTCTC CTGTCTCAGC CTCCCGAGTA GCTGGGACTA CAGGTACGTG      60

CCACCACACC TGGCTAATTT TTGTATTTTT AGTAGAGACA AGAGTTACAC CATATTGGCC    120

AGGATCTTTT GCTTTCTATA GCTTCAAAAT GTTCTTAATG TTAAGACATT CTTAATACTC    180

TGAACCATAT GAATTTGCCA TTTTGGTAAG TCACAGACGC CAGATGGTGG CAATTTCACA    240

TGGCACAACC CGAAAGATTA ACAAACTATC CAGCAGATGA AAGGATTTTT TTTAGTTTCA    300

TTGGGTTTAC TGAAGAAATT GTTTGAATTC TCATTGCATC TCCAGTTCAA CAGATAATGA    360

GTGAGTGATG CCACACTCTC AAGAGTTAAA AACAAAACAA CAAAAAAATT AAAACAAAAG    420

CACACAACTT TCTCTCTCTG TCCCAAAATA CATACTTGCA TACCCCCGCT CCAGATAAAA    480

TCCAAAGGGT AAAACTGTCT TCATGCCTGC AAATTCCTAA GGAGGGCACC TAAAGTACTT    540

GACAGCGAGT GTGCTGAGGA AATCGGCAGC TGTTGAAGTC ACCTCCTGTG CTCTTGCCAA    600

ATGTTTGAAA GGGAATACAC TGGGTTACCG GGTGTATGTT GGGAGGGGAG CATTATCAGT    660

GCTCGGGTGA GGCAAGTTCG GAGTACCCAG ATGGAGACAT CCGTGTCTGT GTCGCTCTGG    720

ATGCCTCCAA GCCAGCGTGT GTTTACTTTC TGTGTGTGTC ACCATGTCTT TGTGCTTCTG    780

GGTGCTTCTG TGTTTGTTTC TGGCCGCGTT TCTGTGTTGG ACAGGGGTGA CTTTGTGCCG    840

GATGGCTTCT GTGTGAGAGC GCGCGCGAGT GTGCATGTCG GTGAGCTGGG AGGGTGTGTC    900

TCAGTGTCTA TGGCTGTGGT TCGGTATAAG TCTGAGCATG TCTGCCAGGG TGTATTTGTG    960

CCTGTATGTG CGTGCCTCGG TGGGCACTCT CGTTTCCTTC CGAATGTGGG GCAGTGCCGG   1020

TGTGCTGCCC TCTGCCTTGA GACCTCAAGC CGCGCAGGCG CCCAGGGCAG GCAGGTAGCG   1080

GCCACAGAAG AGCCAAAAGC TCCCGGGTTG GCTGGTAAGG ACACCACCTC CAGCTTTAGC   1140

CCTCTGGGGC CAGCCAGGGT AGCCGGGAAG CAGTGGTGGC CCGCCCTCCA GGGAGCAGTT   1200

GGGCCCCGCC CGGGCCAGCC CCAGGAGAAG GAGGGCGAGG GGAGGGGAGG GAAAGGGGAG   1260
```

-continued

```
GAGTGCCTCG CCCCTTCGCG GCTGCCGGCG TGCCATTGGC CGAAAGTTCC CGTACGTCAC    1320

GGCGAGGGCA GTTCCCCTAA AGTCCTGTGC ACATAACGGG CAGAACGCAC TGCGAAGCGG    1380

CTTCTTCAGA GCACGGGCTG GAACTGGCAG GCACCGCGAG CCCCTAGCAC CCGACAAGCT    1440

GAGTGTGCAG GACGAGTCCC CACCACACCC ACACCACAGC CGCTGAATGA GGCTTCCAGG    1500

CGTCCGCTCG CGGCCCGCAG AGCCCCGCCG TGGGTCCGCC CGCTGAGGCG CCCCCAGCCA    1560

GTGCGCTTAC CTGCCAGACT GCGCGCCATG GGGCAACCCG GGAACGGCAG CGCCTTCTTG    1620

CTGGCACCCA ATAGAAGCCA TGCGCCGGAC CACGACGTCA CGCAGCAAAG GGACGAGGTG    1680

TGGGTGGTGG GCATGGGCAT CGTCATGTCT CTCATCGTCC TGGCCATCGT GTTTGGCAAT    1740

GTGCTGGTCA TCACAGCCAT TGCCAAGTTC GAGCGTCTGC AGACGGTCAC CAACTACTTC    1800

ATCACTTCAC TGGCCTGTGC TGATCTGGTC ATGGGCCTGG CAGTGGTGCC CTTTGGGGCC    1860

GCCCATATTC TTATGAAAAT GTGGACTTTT GGCAACTTCT GGTGCGAGTT TTGGACTTCC    1920

ATTGATGTGC TGTGCGTCAC GGCCAGCATT GAGACCCTGT GCGTGATCGC AGTGGATCGC    1980

TACTTTGCCA TTACTTCACC TTTCAAGTAC CAGAGCCTGC TGACCAAGAA TAAGGCCCGG    2040

GTGATCATTC TGATGGTGTG GATTGTGTCA GGCCTTACCT CCTTCTTGCC CATTCAGATG    2100

CACTGGTACC GGGCCACCCA CCAGGAAGCC ATCAACTGCT ATGCCAATGA GACCTGCTGT    2160

GACTTCTTCA CGAACCAAGC CTATGCCATT GCCTCTTCCA TCGTGTCCTT CTACGTTCCC    2220

CTGGTGATCA TGGTCTTCGT CTACTCCAGG GTCTTTCAGG AGGCCAAAAG GCAGCTCCAG    2280

AAGATTGACA AATCTGAGGG CCGCTTCCAT GTCCAGAACC TTAGCCAGGT GGAGCAGGAT    2340

GGGCGGACGG GGCATGGACT CCGCAGATCT TCCAAGTTCT GCTTGAAGGA GCACAAAGCC    2400

CTCAAGACGT TAGGCATCAT CATGGGCACT TTCACCCTCT GCTGGCTGCC CTTCTTCATC    2460

GTTAACATTG TGCATGTGAT CCAGGATAAC CTCATCCGTA AGGAAGTTTA CATCCTCCTA    2520

AATTGGATAG GCTATGTCAA TTCTGGTTTC AATCCCCTTA TCTACTGCCG GAGCCCAGAT    2580

TTCAGGATTG CCTTCCAGGA GCTTCTGTGC CTGCGCAGGT CTTCTTTGAA GGCCTATGGG    2640

AATGGCTACT CCAGCAACGG CAACACAGGG GAGCAGAGTG GATATCACGT GGAACAGGAG    2700

AAAGAAAATA AACTGCTGTG TGAAGACCTC CCAGGCACGG AAGACTTTGT GGGCCATCAA    2760

GGTACTGTGC CTAGCGATAA CATTGATTCA CAAGGGAGGA ATTGTAGTAC AAATGACTCA    2820

CTGCTGTAAA GCAGTTTTTC TACTTTTAAA GACCCCCCCC CCCCCAACAG AACACTAAAC    2880

AGACTATTTA ACTTGAGGGT AATAAACTTA GAATAAAATT GTAAAAATTG TATAGAGATA    2940

TGCAGAAGGA AGGGCATCCT TCTGCCTTTT TTATTTTTTT AAGCTGTAAA AAGAGAGAAA    3000

ACTTATTTGA GTGATTATTT GTTATTTGTA CAGTTCAGTT CCTCTTTGCA TGGAATTTGT    3060

AAGTTTATGT CTAAAGAGCT TTAGTCCTAG AGGACCTGAG TCTGCTATAT TTTCATGACT    3120

TTTCCATGTA TCTACCTCAC TATTCAAGTA TTAGGGGTAA TATATTGCTG CTGGTAATTT    3180

GTATCTGAAG GAGATTTTCC TTCCTACACC CTTGGACTTG AGGATTTTGA GTATCTCGGA    3240

CCTTTCAGCT GTGAACATGG ACTCTTCCCC CACTCCTCTT ATTTGCTCAC ACGGGGTATT    3300

TTAGGCAGGG ATTTGAGGAG CAGCTTCAGT TGTTTTCCCG AGCAAAGGTC TAAAGTTTAC    3360

AGTAAATAAA ATGTTTGACC ATGCCTTCAT TGCACCTGTT TGTCCAAAAC CCCTTGACTG    3420

GAGTGCTGTT GCCTCCCCCA CTGGAAACCG C                                   3451
```

(2) INFORMATION FOR SEQ ID NO:3:

(i) SEQUENCE CHARACTERISTICS:

(A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: wild-type forward primer A1

(xi) SEQUENCE DESCRIPTION: SEQ ID NO:3:

GCCTCTTGCT GGCACCCAAA A                                         21

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: polymorphism-specific primer A2

(xi) SEQUENCE DESCRIPTION: SEQ ID NO:4:

GCCTTCTTGC TGGCACCCAA AG                                        22

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: reverse primer Rev (xi) SEQUENCE DESCRIPTION: SEQ ID NO:5:

AGGATAACCT CATCCGTAAG G                                         21

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: wild-type forward primer B1

(xi) SEQUENCE DESCRIPTION: SEQ ID NO:6:

CCGGACCACG ACGTCACGCA AC                                        22

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

-continued

```
    (vii) IMMEDIATE SOURCE:
         (B) CLONE: polymorphism-specific formward primer B2

(xi) SEQUENCE DESCRIPTION: SEQ ID NO:7:

CCGGACCACG ACGTCACGCA AG                                                   22

(2) INFORMATION FOR SEQ ID NO:8:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: Beta-golbin forward primer BG1

(xi) SEQUENCE DESCRIPTION: SEQ ID NO:8:

GCTGTCATCA CTTAGACCTC                                                      20

(2) INFORMATION FOR SEQ ID NO:9:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: Beta-globin reverse primer BG2

(xi) SEQUENCE DESCRIPTION: SEQ ID NO:9:

CAGACGAATG ATTGCATCAG                                                      20
```

DIAGNOSING ASTHMA PATIENTS PREDISPOSED TO ADVERSE β-AGONIST REACTIONS

GOVERNMENT SUPPORT

Development of the present invention was supported in part by National Institutes of Health grants numbered U10 HL 51831, U10 HL 51834, U10 HL 51843, U10 HL 51810, U10 HL 51823, and U10 HL 51845. The United States Government may have certain rights in the invention.

BACKGROUND OF THE INVENTION

Inhaled medium acting β-agonists are the most commonly prescribed asthma treatments in the world. β-agonists produce their effects by stimulating the $β_2$-adrenergic receptors on cells and thereby activating intracellular pathways that produce increased levels of cyclic adenosine monophosphate (cAMP). The increased intracellular cAMP levels in turn produce macroscopic effects in the cells, relaxing the smooth muscles of the bronchial airways, increasing ciliary beat frequency, and reducing mucous viscosity. The effectiveness of β-agonists at dilating bronchial airways has led to their widespread administration both as a treatment for acute asthmatic episodes and as a long-term asthma management therapy.

Concerns about the safety of β-agonist therapy have arisen periodically over the years (reviewed in, for example, Taylor et al., *Med. Clin. N. America* 80:719, 1996; Giunti et al., *Eur. Respir. J.* 8:673, 1995; Barrett et al., *Am. J. Respir. Crit. Care Med.* 151:574, 1995; Devoy et al., *Chest* 107:1116, 1995; McFadden, *Ann. Allergy Asthma Immunol.* 75:173, 1995; Crane et al., *Thorax* 50:S5, 1995; McFadden, *J. Allergy Clin. Immunol.* 95:41, 1995). Reports of possible associations between β-agonist administration and increased morbidity, particularly for chronic β-agonist administration protocols, have spurred much debate over the safety of β-agonist therapy. There is a need to resolve this debate and to identify risks of deleterious or salutory effects associated with administration of β-agonists to asthmatics.

SUMMARY OF THE INVENTION

The present invention resolves the debate over the safety of β-agonist therapy and identifies a population of asthmatic patients who are at risk for an adverse reaction to regular administration of β-agonists. In particular, the present invention provides the discovery that asthmatics who carry a particular allele of the $β_2$-adrenergic receptor gene are more likely to have a negative response to chronic β-agonist therapy. The present invention provides methods of identifying individuals at risk for an adverse response to β-agonist treatment, and also provides diagnostic kits useful in the practice of such methods.

In preferred embodiments of the methods of the present invention, a genomic nucleic acid sample is provided from an individual, first and second $β_2$-adrenergic receptor gene alleles are identified within the genomic nucleic acid sample, and any individual for whom both the first and second $β_2$-adrenergic receptor gene alleles encode Arg at residue 16 is classified as being at risk for adverse reaction to chronic β-agonist administration. The particular method by which the $β_2$-adrenergic receptor gene alleles are identified within the genomic sample is not intended to limit the scope of the present invention. However, preferred identification methods include allele-specific polymerase chain reaction (PCR) techniques and direct sequencing techniques.

Preferred kits provided by the practice of the present invention include reagents useful for performing the inventive methods, which reagents are assembled together in a container for ease of use.

DESCRIPTION OF THE SEQUENCES

Figure 1:
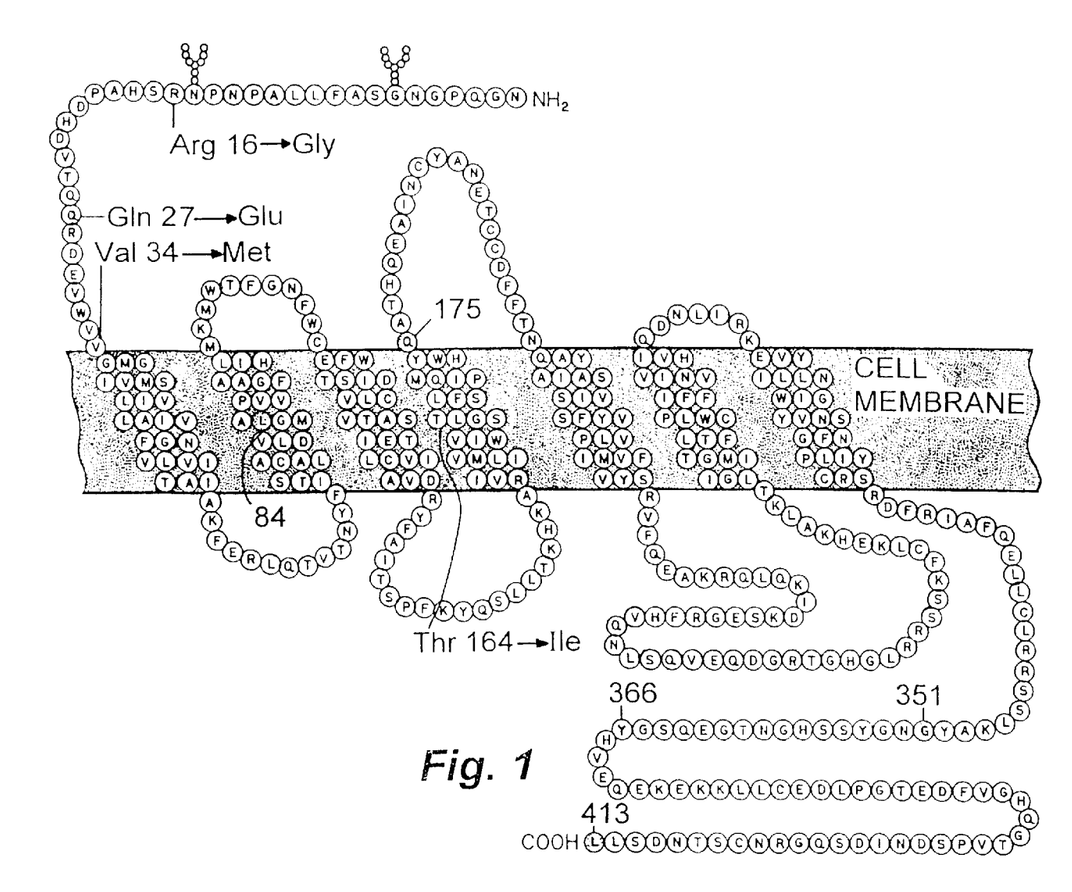
FIG. 1 depicts the primary amino acid sequence and known polymorphic sites in the human $β_2$-adrenergic receptor protein. Nine polymorphic sites are shown; those shown in black represent different gene alleles that encode the same residue, whereas those in white that are labeled with alternate amino acids represent gene alleles that result in residue substitutions.

SEQ ID NO:1 presents an amino acid sequence of the $β_2$-adrenergic receptor. In SEQ ID NO:1, Arg, Gln, Val, and Thr are located at positions 16, 27, 34, and 164, respectively. Known gene polymorphisms produce $β_2$-adrenergic receptors with Gly, Glu, Met, and Ile, respectively, at these positions (see FIG. 1).

SEQ ID NO:2 presents a human $β_2$-adrenergic receptor gene encoding the protein of SEQ ID NO: 1. The Arg16→Gly polymorphism described above with respect to SEQ ID NO: 1 can be produced by substituting a G for the A at SEQ ID NO:2 position 1633; the Gln 27→Glu polymorphism can be produced by substituting a G for the C at 1666.

DESCRIPTION OF PREFERRED EMBODIMENTS

The human gene for the $β_2$-adrenergic receptor has been cloned (Kobilka et al., *Proc. Natl. Acad. Sci. USA* 84:46, 1987) and extensively studied. Nine gene polymorphisms have been identified in the general population, four of which result in amino acid substitutions (the other five are silent changes) (see FIG. 1; see also, Reihsaus et al., *Am. J. Respir. Cell. Mol. Biol.* 8:334, 1993). The present invention relates to the "Arg16→Gly" polymorphism depicted in FIG. 1.

Various studies have been undertaken to identify any significance of the Arg16→Gly polymorphism in asthma (for review, see Liggett, Chapter 21, *The Genetics of Asthma* [Liggett et al., eds], Marcel Dekker, NY, 1996). No general association between either the Arg16 or the Gly16 allele and asthma has been observed (Reihsaus et al., *Am. J. Respir. Cell. Mol. Biol.* 8:334, 1993). Also, the Arg16 and the Gly16 proteins have been shown to have equivalent affinities for agonists and antagonists, and to couple normally to $G_1$ (Green et al., *Biochemistry* 33:9414, 1994).

The only difference observed prior to the present invention between the Arg16 and Gly16 allele was enhanced down regulation of the Gly16 allele in response to β-agonist administration (Green et al., *Biochemistry* 33:9414, 1994). This finding prompted one expert in the field to conclude that:

> "the Gly16 variant, which undergoes the greatest degree of agonist promoted down regulation, would be expected to display an overall reduced level of expression as compared with [the Arg16 variant]. Under this scenario, basal bronchomotor tone might be decreased or bronchial hyperactivity increased .... Responsiveness to β-agonist may also be depressed in asthmatics harboring [the Gly16] polymorphism .... During chronic agonist therapy, the potential for tachyphylaxis would appear to be greatest with the Gly16 variant .... Given reports that suggest a relationship between 'overuse' of β-agonists and adverse outcomes in asthma, it seems prudent to consider that tachyphylaxis may occur in some individuals"

(citations omitted; Ligget, Chapter 21, *The Genetics of Asthma* (Ligget et al., eds), Marcel Dekker, NY, 1996, pg. 470). Thus, prior to the present invention, the state of knowledge concerning the Arg16→Gly polymorphism in the human $\beta_2$-adrenergic receptor indicated that individuals carrying the Gly16 allele might suffer more tachyphylaxis in response to chronic β-agonist therapy, and therefore might be more susceptible to adverse responses to β-agonist administration.

Surprisingly, the present invention provides the discovery that the opposite is true: individuals carrying the Gly16 allele of the human $\beta_2$-adrenergic receptor are actually less susceptible to adverse responses to β-agonist administration. According to the present invention, individuals who are homozygous for the Arg16 allele are more likely to have an adverse response to β-agonist therapy than either Gly16 homozygotes or Gly16/Arg16 heterozygotes. It will be appreciated by those skilled in the art that this method of identifying individuals more likely to have an adverse response to β-agonist therapy will be applicable whether the β-agonist therapy administered comprises a racemic or enantiomeric form of the chosen β-agonist.

Figure 2:
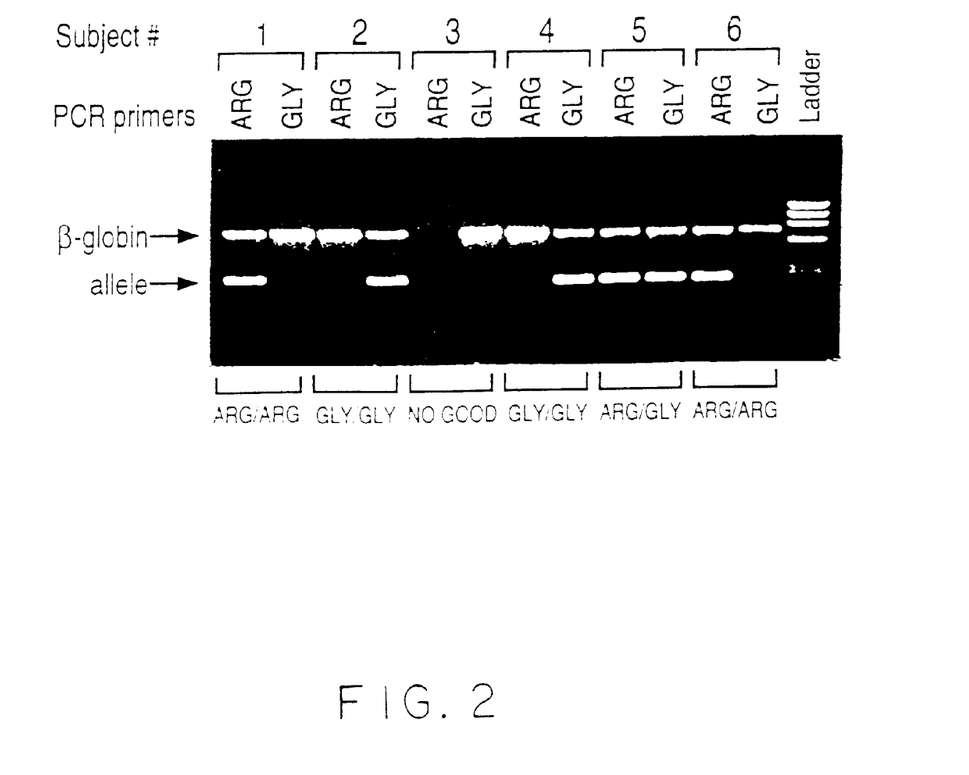
FIG. 2 is a photograph of an agarose gel presenting genotype analyses of six BAGS patients at residue 16 of the $β_2$ adrenergic receptor.

As described in Example 2, we analyzed the $\beta_2$-adrenergic receptor genotype in 179 subjects who had participated in a study testing their response to regular and as-needed albuterol administration (Drazen et al., *New Eng. J. Med.* 335:841, 1996, incorporated herein by reference; see also Example 1). That study had concluded that "in patients with mild asthma, neither deleterious nor beneficial effects derived from the regular use of inhaled albuterol beyond those derived from the regular use of the drug as needed (Drazen et al., id.). When we examined the $\beta_2$-adrenergic receptor genotype in the study participants, however, we came to a rather different conclusion. FIG. 2 shows our findings: individuals who carry two copies of the Arg16 $\beta_2$-adrenergic receptor allele showed significant decreases in peak expiratory flow rate (PEFR) after receiving regular β-agonist therapy for 16 weeks. Gly16 homozygotes and Arg16/Gly16 heterozygotes did not show this effect. Arg16 homozygotes who received β-agonist treatments on an as-needed basis showed more modest decreases in PEFR and these decreases were only temporary.

By demonstrating a correlation between adverse response to chronic β-agonist therapy and the presence of (two copies of) the Arg16 $\beta_2$-adrenergic receptor allele, the present invention provides methods for identifying asthmatic patients at risk of such an adverse response. Quite simply, patients are screened to identify the $\beta_2$-adrenergic receptor alleles they carry; those who are homozygous for Arg16 are identified as susceptible. Any available method can be used to detect patients' $\beta_2$-adrenergic receptor genotype (see, for example, Examples 2 and 3; see also methods described in *Current Protocols in Human Genetics,* John Wiley & Sons, Unit 9, incorporated herein by reference).

For example, the relevant region of each patients' $\beta_2$-adrenergic receptor gene (both alleles) can be directly sequenced according to known techniques. Alternatively or additionally, techniques such as denaturing gradient gel electrophoresis, allele-specific polymerase chain reaction (PCR), allele-specific hybridization, allele-specific ligation amplification (see, for example, English et al., *Proc. Natl. Acad. Sci. USA* 9:360, 1994, incorporated herein by reference), single strand conformation polymorphism analysis, restriction fragment length polymorphism analysis, or any other available technique useful to distinguish sequence polymorphisms may be employed. Allele-specific PCR techniques, such as the amplification refractory mutation system (ARMS), or amplification followed by sequencing, are preferred methods of polymorphism detection. Preferred hybridization methods include hybridization to oligonucleotides on a silica chip array (see, for example, Hacia et al, *Nature Genetics* 14:441, 1996, incorporated herein by reference; see also *Nature Genetics* 14:367, 1996).

The present invention also provides kits for identifying asthma patients susceptible to adverse responses to chronic β-agonist administration. Preferred kits comprise reaction components useful for allele-specific PCR techniques. For example, particularly preferred kits include primer sets capable of amplifying and distinguishing the Arg16 and Gly16 alleles, and may also include buffers, thermalstable reverse transcriptase, control templates, etc. Alternative preferred kits include amplification reagents that are not necessarily allele-specific, in combination with sequencing reagents.

EXAMPLES

Example 1

Analysis of Beneficial and Deleterious Effects of Regularly-Scheduled and As-Needed Albuterol Administration in Patients with Mild Asthma (see Drazen et al., *NEJM* 335:841, 1996, incorporated herein by reference)

Materials and Methods

PATIENT RECRUITMENT: Patients with mild asthma, as defined by the criteria shown in Table 1, were recruited from existing study populations and by advertising. Eligible patients entered a six-week single-blind run-in period, during which they used a placebo inhaler on a regular basis (two inhalations four times a day) and took supplemental puffs of open-label albuterol as needed. During the run-in period, patients were evaluated three times at two-week intervals, at which time asthma control was assessed by the review of a number of criteria.

TABLE 1

CHARACTERISTICS USED TO DEFINE MILD ASTHMA*

| CHARACTERISTIC | ALLOWABLE RANGE |
|---|---|
| $FEV_1$† | ≧70% of predicted value |
| Age | 12 to 55 yr |
| $PC_{20}$ | ≦16 mg/ml |

TABLE 1-continued

CHARACTERISTICS USED TO DEFINE MILD ASTHMA*

| CHARACTERISTIC | ALLOWABLE RANGE |
| --- | --- |
| Use of β-agonists | 6 to 56 puffs of albuterol/wk; patients using less than 6 puffs of albuterol/wk at visit 1 had to have a $PC_{20}$ of $\leq 8$ mg/ml |
| Use of other asthma medications | None, no corticosteroids for 6 wk |
| Other serious medical conditions, including pregnancy | Not allowed |
| Smoking | None in past year, maximal history of 5 pack-years permitted |

*$FEV_1$ denotes forced expiratory volume in one second, and $PC_{20}$ the concentration of methacholine required to decrease the $FEV_1$ by 20 percent.
†The $FEV_1$ was measured after at least eight hours without bronchodilator medications.

PATIENT SELECTION: Patients were randomly assigned to a treatment group if over the six-week period their asthma was clinically stable and they demonstrated their ability to comply with the study procedures, as indicated by the regular use of the placebo inhaler (monitored by a Chronology recording device) and their ability to record their peak flow (twice daily, using a Mini-Wright peak-flow meter) (Clement Clarke, Columbus, Ohio) and asthma symptoms once daily in a diary. The treatments assigned consisted of either inhaled albuterol on a regular basis (two inhalations four times a day) plus albuterol as needed or inhaled placebo on a regular basis (two inhalations four times a day) plus albuterol as needed. Albuterol and placebo inhalers were generously supplied by Schering-Plough (Memphis, Tenn.). Patients were instructed to have their regularly scheduled inhalations in the morning after recording their morning peak flow, at midday, in the late afternoon, and on retiring to sleep after recording their evening peak flow. They were instructed to allow at least four hours between their regularly scheduled inhalation in the late afternoon and the recording of their evening peak flow.

PATIENT TREATMENT: Over the ensuing 16 weeks, while patients received blinded treatment, the control of asthma was monitored daily, through peak flow rates and symptoms recorded by patients, as well as during clinic visits, which were scheduled every two to three weeks. At the completion of the randomized-treatment period, all the patients were switched to single-blind treatment with inhaled placebo for a four-week withdrawal period; during this time patients continued to use open-label albuterol as needed.

Seven outcome indicators were monitored: peak flow, the symptom record, quality of life, the change in the forced expiratory volume in one second ($FEV_1$) in response to an inhaled bronchodilators, the concentration of methacholine required to decrease the $FEV_1$ by 20 percent ($PC_{20}$), asthma exacerbations, and treatment failure.

Peak flow, the primary outcome indicator, was measured twice daily by patients using a Mini-Wright peak-flow meter; the best of three efforts was recorded. Patients recorded their asthma symptoms and the number of puffs of supplemental albuterol used daily. Asthma symptoms were recorded on a 4-point scale, with 0 representing no symptoms and 3 representing severe symptoms. Asthma-specific quality-of-life scores were recorded during clinic visits, with an instrument validated by other investigators (Juniper et al., Thorax 47:76, 1992). To determine the spirometric response to an inhaled bronchodilator, the difference in the $FEV_1$ before and 15 minutes after two inhalations of albuterol was measured (and reported as percent improvement) during clinic visits when responsiveness to methacholine was not tested.

Patients refrained from taking their study medications for at least eight hours before all clinic visits. To measure $PC_{20}$ for methacholine, methacholine aerosols were generated with a nebulizer (model 646, DeVilbiss Health Care, Somerset, Pa.) and a calibrated dosimeter (S&M Instruments, Dovestown, Pa.). The $PC_{20}$ for methacholine was determined by standard procedures (Tashkin et al., Am. Rev. Respir. Dis. 145:301, 1992). Asthma exacerbations were monitored during each clinic visit; patients were asked about their asthma control, and all asthma exacerbations were recorded. An asthma exacerbation was defined as an increase in symptoms of cough, chest tightness, or wheezing in association with one or more of the following; an increase over the base-line use of supplemental β-agonist treatments of 8 or more puffs per 24 hours for a period of 48 hours, the use of 16 or more puffs of a supplemental β-agonist per 24 hours for a period of 48 hours, or a fall in peak flow of 35 percent or more from the best three-day average (morning and evening) during the run-in period.

Treatment was considered to have failed if patients who had asthma exacerbations and were treated with increased doses of β-agonists did not respond adequately—that is, if they continued to meet the criteria for exacerbation. Such patients were treated with a short course of prednisone, as determined by their physicians; their data continued to be collected, and they remained in the trial (in accordance with the intention-to-treat method).

STANDARDIZATION AND QUALITY-ASSURANCE TECHNIQUES: All clinical laboratory tests—that is, measurements of lung function, skin testing for allergies, methacholine challenges, and quality-of-life assessments—were performed at each center with the use of equipment and procedures that were standardized for the entire network. Workers participating in the network were tested to ensure proficiency and uniformity in all network-related skills and had to pass certification examinations before the data they gathered could be used in the network. All results of spirometric testing (Collins Eagle 2 spirometer, Quincy, Mass.), including that for the methacholine challenge, were confirmed by a single network member. Peak-flow meters were tested against spirometers during each clinic visit and were replaced if they failed to meet previously established performance standards. A distributed data-entry system allowed each clinical center to submit its data over the Internet directly to the Data Coordinating Center. The Data Coordinating Center entered the data a second time to verify it.

COMPLIANCE: Each patient was given a digital wristwatch with multiple alarms to improve treatment compliance. In addition, Chronology recording devices were used with the randomly assigned metered-dose inhalers to provide an electronic record of the date and time of inhaler use.

STATISTICAL ANALYSIS: Morning peak flow was chosen as the primary outcome variable for the calculation of sample size. A Minimum of 200 patients made it possible to detect a difference of 25 liters per minute between groups with 80 percent statistical power. A goal of recruiting 250 randomized patients was established on the assumption that the dropout rate would be less than 20 percent. This sample size also provided 80 percent statistical power to detect a difference of 0.19 liter in $FEV_1$ and 0.70 doubling dilution in the $PC_{20}$ values for methacholine.

Response variables—that is, peak-flow values, medication use, and asthma symptoms—from the patients' diary cards were averaged each week. Because of the longitudinal nature of most of the response variables, a mixed-effects linear model was applied (Vonesh et al., *Biometrics* 43:617, 1987; Laird et al., *Stat Methods Med Res* 1:225, 1992); this approach allowed all data obtained to be used, not just the data obtained at a single visit. For each response variable, a segmented linear model was fitted with an intercept and with slopes for the last 4 weeks of the run-in period, the first 5 weeks of the treatment period, the remaining 11 weeks of the treatment period, and the withdrawal period. The "break point" after five weeks of randomized treatment was chosen on the basis of rates of asthma exacerbation reported by Sears et al. (Sears et al., *Lancet* 336:1391, 1990).

For each outcome measure, values were calculated from the models for the end of the run-in period, for the end of the double-blind-treatment period, and for the end of the withdrawal period. This statistical model was determined before the start of the study, and therefore other models were not considered during data analysis. The groups were compared with respect to rates of treatment failure with the use of Fisher's exact test. To ensure patient safety, an interim analysis was conducted after approximately 40 percent of the randomized patients had completed the trial or withdrawn consent; as a result of this analysis, the P value considered to indicate statistical significance was reduced from 0.05 to 0.03 for the final analyses (Pocock, *Biometrics* 38:153, 1982; Geller et al., *Biometrics* 43:213, 1987).

Results

ENROLLMENT AND RETENTION: Of the subjects recruited, 255 were eligible for enrollment at the end of the six-week run-in period and were randomly assigned to receive double-blind treatment (Table 2). There were no significant differences between the treatment groups with respect to any of the indexes monitored. During the period of randomized treatment and withdrawal, 25 subjects dropped out of the trial—10 in the scheduled-treatment group and 15 in the treatment-as-needed group. Two hundred thirty patients completed the entire trial.

TABLE 2

CHARACTERISTICS OF PATIENTS IN THE TWO TREATMENT GROUPS

| CHARACTERISTIC* | ALBUTEROL TREATMENT† | |
|---|---|---|
| | REGULARLY SCHEDULED (n = 126) | AS-NEEDED ONLY (N = 129) |
| Male sex - no. (%) | 57 (45.2) | 55 (42.6) |
| Minority racial or ethnic group - no. (%)‡ | 41 (32.5) | 43 (33.3) |
| Atophy - no. (%) | 122 (96.8) | 127 (98.4) |
| Age - yr | 28.6 ± 9.0 | 29.3 ± 9.2 |
| Age <18 yr - no. (%) | 16 (12.7) | 10 (7.8) |
| Morning peak flow - liters/min§ | 418.3 ± 100.5 | 421.6 ± 99.8 |
| Evening peak flow - liters/min§ | 437.6 ± 101.5 | 440.7 ± 99.1 |
| Peak-flow variability - %§¶ | 3.9 ± 5.7 | 3.7 ± 6.9 |
| Symptom score§‖ | 0.46 ± 0.40 | 0.38 ± 0.34 |
| No. of supplemental puffs of β-agonist per day§ | 1.5 ± 2.0 | 1.7 ± 2.2 |
| $FEV_1$ - liters¶ (% of predicted value)** | 3.1 ± 0.74 (89.0 ± 12.7) | 3.15 ± 0.68 (91.4 ± 13.9) |
| Quality-of-life score**†† | 2.28 ± 0.82 | 2.44 ± 0.82 |

TABLE 2-continued

CHARACTERISTICS OF PATIENTS IN THE TWO TREATMENT GROUPS

| CHARACTERISTIC* | ALBUTEROL TREATMENT† | |
|---|---|---|
| | REGULARLY SCHEDULED (n = 126) | AS-NEEDED ONLY (N = 129) |
| $PC_{20}$ - mg/m²**‡‡ | 0.64 ± 1.82 | 0.64 ± 1.82 |
| $FEV_1$ response to albuterol inhaiation - % change from base line §§ | 10.5 ± 8.3 | 10.8 ± 9.2 |

*$FEV_1$ denotes forced expiratory volume in one second, and $PC_{20}$ the concentration of methacholine required to decrease the $FEV_1$ by 20 percent.
†Plus-minus values are means ± SD unless otherwise indicated.
‡Fifty-nine percent of the minority patients in the scheduled group were black, and 65 percent in the as-needed group were black.
§Values represent averages for the last four weeks of the run-in period.
¶Peak-flow variability was calculated as ([evening peak flow − morning peak flow] ÷ evening peak flow) × 100.
‖Asthma symptoms were graded by the patient each day, from 0 for no symptoms to 3 for incapacitating symptoms.
**This characteristic was measured from week 6 of the run-in period.
††Asthma-specific quality-of-life questionnaires were completed by the patients during clinical-center visits. A score of 1.0 indicates that asthma had no effect on the overall quality of life; a score of 2.0, that the patient's life was "a little limited" by asthma; a score of 3.0, that there was "some limitation"; and a score of 7.0, that there was "total limitation."
‡‡Values are medians and interquartile ranges.
§§Data are the averages from weeks 2 and 4 of the run-in period.

COMPLIANCE: Compliance with the use of inhaled medication, either active or placebo, on a regular basis was greater than 80 percent, as indicated by Chronolog treatment records and an analysis of diary cards. Of the 3172 scheduled visits to patients' clinical center, 26 were missed, for a rate of compliance of over 99 percent.

ASTHMA EXACERBATIONS: Asthma was exacerbated 24 times (11 times in the scheduled-treatment group and 13 times in the treatment-as-needed group) during the active treatment period and 4 times during the withdrawal period (twice in each treatment group). The 28 exacerbations occurred in 12 patients in the scheduled-treatment group and 11 patients in the treatment-as-needed group.

TREATMENT FAILURES: Treatment was considered to have failed in 11 patients during the 16-week period of randomized treatment (5 in the scheduled-treatment group and 6 in the treatment-as-needed group) and in 2 during the withdrawal period (both in the scheduled-treatment group). There were three visits to the emergency room for asthma (two in the scheduled-treatment group and one in the treatment-as-needed group). No patients were hospitalized for asthma during the trial, and none died. There were no significant differences in any of the event rates between the two treatment groups.

EFFICACY OUTCOMES: Lung function (indicated by morning peak flow, evening peak flow, peak-flow variability, $FEV_1$, β-agonist responsiveness, and $PC_{20}$) and asthma symptoms (determined by the number of uses of the supplemental β-agonists metered-dose inhalers, diary scores and quality-of-life scores) as derived from the regression analysis performed for each patient group are shown in Table 3. Graphic displays of values predicted by the model as compared with sample means showed excellent goodness of fit by the statistical model (data not shown). There were no significant differences in morning peak flow between the two treatment groups (Table 3). Even though the average use of albuterol was 9.3 puffs per day in the scheduled-use group and 1.6 puffs per day in the treatment-as-needed group, the extra use of medication did not lead to differences in peak-flow variability, $FEV_1$, supplemental albuterol use, asthma symptoms, quality of life, or $PC_{20}$.

Two significant differences were found between the groups. Once was in the change in evening peak flow from the end of the treatment period to the end of the withdrawal period; mean evening peak flow fell 17.7 liters per minute in the scheduled-treatment group but increased 1.3 liters per minute in the treatment-as-needed group. The other significant difference was in the change in bronchodilator responsiveness between the run-in period and the treatment period (Table 3). The $FEV_1$ response to treatment with albuterol increased from a 10.7 percent improvement to a 12.5 percent improvement in the scheduled-treatment group and decreased from a 10.7 percent improvement to a 9.2 improvement in the treatment-as-needed group. A number of small but statistically significant changes within the groups were noted among the various treatment periods, as shown in Table 3. Results of the analysis in which data collected after the subjects in whom treatment was considered to have failed were excluded were essentially the same as those derived with the use of the intention-to-treat method.

TABLE 3

MODEL ESTIMATES (USING INTENTION-TO-TREAT DATA) FOR THE END OF THE RUN-IN PERIOD (WEEK 6), THE END OF THE ACTIVE-TREATMENT PERIOD (WEEKS 22), AND THE END OF THE WITHDRAWAL PERIOD (WEEK 26).*

| OUTCOME† | AFTER RUN-IN PERIOD | | AFTER TREATMENT PERIOD | | AFTER WITHDRAWAL PERIOD | |
|---|---|---|---|---|---|---|
| | SCHEDULED | AS NEEDED | SCHEDULED | AS NEEDED | SCHEDULED | AS NEEDED |
| Peak flow (liters/min) | | | | | | |
| Morning | 415.9 | 424.1 | 414.4 | 424.5 | 414.8 | 427.3 |
| Evening | 436.3 | 441.1 | 441.3 | 445.2 | 433.6 P = 0.005‡ P = 0.021§ | 446.5 |
| Peak-flow variability (%)¶ | 4.1 | 3.2 | 5.7 P < 0.001‖ | 4.3 | 4.0 P < 0.001‡ | 4.2 |
| $FEV_1$ (liters) | 3.09 | 3.13 | 3.04 | 3.12 | 3.06 | 3.12 |
| Albuterol response (%)** | 10.7 | 10.7 | 12.5 P = 0.005†† | 9.2 | | |
| Extra albuterol (puffs/day) | 1.4 | 1.6 | 1.3 | 1.6 | 1.6 P = 0.013‡ | 1.6 |
| Symptom score‡‡ | 0.4 | 0.4 | 0.4 | 0.4 | 0.4 | 0.4 |
| Quality-of-life score‡‡ | 2.3 | 2.4 | 2.3 | 2.3 | 2.1 P = 0.003‡ P = 0.006§ | 2.2 P = 0.008§§ |
| $PC_{20}$ (mg/ml) | 0.73 | 0.73 | 0.56 p = 0.013‖ | 0.72 | 0.66 | 0.76 |

*Values differ from those in Table 2 because Table 2 contains the mean data rather than estimates from the model.
†$FEV_1$ denotes forced expiratory volume in one second, and $PC_{20}$ the concentration of methacholine required to decrease the $FEV_1$ by 20 percent.
‡P value is for the within-group comparison of the response at the end of the treatment period with that at the end of the withdrawal period.
§P value is for the comparison between groups of the change in response from the end of the treatment period to the end of the withdrawal period.
§Peak-flow variability was calculated as ([evening peak flow − morning peak flow] ÷ evening peak flow) × 100 (Martin et al., Am. Rev. Respir. Dis. 143:351, 1991).
‖P value is for the within-group comparison of the response at the end of the treatment period with that at the end of the run-in Period.
**Bronchodilator response was last measured during the run-in period at week 4 and during the active-treatment period at week 20.
††P value is for the comparison between groups of the change in response from the end of the run-in period to the end of treatment period.
‡‡See the footnotes to Table 2 for an explanation of the scoring system.
§§P value is for the within-group comparison of the response at the end of the run-in period with that at the end of the withdrawal period.

These results show that regular use of inhaled albuteral in patients with mild asthma is not generally associated with a deleterious effect on asthma control.

Example 2

Correlation of $\beta_2$-Adrenergic Receptor Allele with Outcome of β-Agonist Administration Materials and Methods:

GENERALLY: The patients analyzed in the present study had been participants in a β-agonist study, referred to as BAGS, sponsored by the Asthma Clinical Research Network of the United States National Heart, Lung and Blood Institute (ACRN). The results of that study are published in the *New England Journal of Medicine* (Drazen et al., *NEJM* 335:841, 1996, incorporated herein by reference); relevant portions of the Materials and Methods and Results sections of that paper are reproduced in Example 1. As noted above, that study concluded that, overall, no negative effects were associated with regular administration of albuterol to mild asthmatics.

We decided to further analyze the results of the BAGS trial by investigating the genotype of study participants' $\beta_2$-adrenergic receptor gene (encoding residue 16 of the protein). We were able to obtain materials for determining each patient's genotype for 179 of the 255 subjects. The remaining subjects either refused to participate or could not be located for genotyping.

ARMS ASSAY: The primers used to detect the $\beta_2$-adrenergic receptor gene polymorphism (corresponding to an A→G substitution at nucleotide 1633 of SEQ ID NO:2) (A→G) that gives rise to the Arg 16→Gly amino acid change in the protein were: Wild-type forward primer A1 (5'-GCCTCTTGCTGGCACCCAA-AA-3' [SEQ ID NO:3]) corresponding to nucleotides 1612–1633, except the penultimate base at the 3' end (underlined) was changed from T to A, polymorphism-specific forward primer A2 (5'-GCCTTCTTGCTGGCACCCAAAG-3' [SEQ ID NO:4], differs from the wild-type primer at the last nucleotide at 3' end (shown in bold), reverse primer Rev (5'-AGGATAACCTCATCCGTAAGG-3' [SEQ ID NO:5]) corresponding to nucleotides 2483–2503 on the complementary strand.

The primers used to detect the $\beta_2$-adrenergic receptor gene polymorphism (corresponding to a C→G substitution at nucleotide 1666 of SEQ ID NO:2) that gives rise to the Gln27→Glu amino acid change in the protein were: Wild-type forward primer B1 (5'-CCGGACCACGACGTCACGCAAC-3' [SEQ ID NO:6] corresponding to nucleotides 1645–1666, except the penultimate base at the 3' end (underlined) was changed from G to A, polymorphism-specific forward primer B2 (5'-CCGGACCACGACGTCACGCAAG-3' [SEQ ID NO:7]), differs from the wild-type primer at the last nucleotide at 3' end (shown in bold), and reverse primer Rev.

Amplification by PCR of the genomic DNA of each sample included two reactions for each assay separately: one with wild type primers (A1 and REV) and the other with polymorphic (A2 and Rev) allele-specific primer set for polymorphism detection at nucleotide 16633 and wild type primers (B1 and Rev) and the polymorphic allele-specific primer set (B2 and Rev) for polymorphism detection at nucleotide 1666. Both polymorphism detection assays included human $\beta$-globin primer sets as positive controls in the PCR reaction mix. The primers for $\beta$-globin were: Forward primer BG1 (5'-GCTGTCATCACTTAGACCTC-3' [SEQ ID NO:8] corresponding to nucleotides 43–62 (Genbank accession no. 148217), reverse primer BG2 (5'-CAGACGAATGATTGCATCAG-3' [SEQ ID NO: 9]) corresponding to nucleotides 766–785 on the complementary strand (Genbank accession no. L48217).

Each PCR reaction contained 5 $\mu$l template DNA (buccal cell lysate or 100–200 ng of blood genomic DNA), PCR buffer II (Perkin Elmer), 1.5mM MgCl$_2$ (Perkin Elmer), 12.5 pmoles of each primer, 400 $\mu$M dNTPs (Perkin Elmer), 0.625 units of Taq polymerase (AmpliTaq polymerase, Perkin Elmer), 0.05 units of Perfect Match PCR enhancer (Stratagene) in a total volume of 25 $\mu$l. Conditions for PCR were: an initial hot start period of 5 min at 94° C., and temperature was hold at 80° C. after the hot start during this period dNTPs and Taq polymerase were added. This was followed by 35 cycles of 1 min at 94° C., 1 min at 58° C., 1 min at 72° C., with a final extension time of 5 min at 72° C. Thin walled 96 micro-well plates (Costar) were used with mineral oil for amplification reactions, in a PTC-100 thermal cycler (MJ Research, Watertown, Mass.). After amplification, about 20 $\mu$l of reaction mixture was resolved by electrophoresis on a 2.0% agarose gel and stained with ethidium bromide for analysis.

Results

Figure 3A:
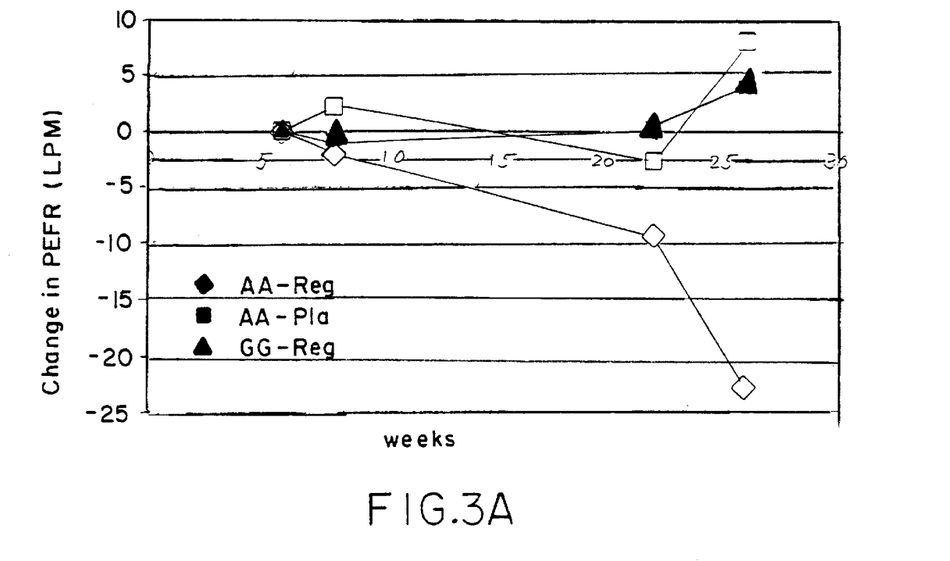
FIG. 3 has panels A and B, showing the morning and afternoon peak expiratory flow rates (PEFR), respectively, of asthmatics who received regularly-scheduled or as-needed albuterol treatments. In each panel, the results are plotted by $β_2$-adrenergic receptor genotype. Data from asthmatics who are homozygous for the $β_2$-adrenergic receptor Arg16 variant are plotted either as a solid line punctuated with diamonds (those who received regular treatment) or a gray line punctuated by squares (those who received as-needed treatment); data from Gly16 homozygotes who received regular treatment are plotted as a light gray line punctuated by triangles.
Figure 3B:
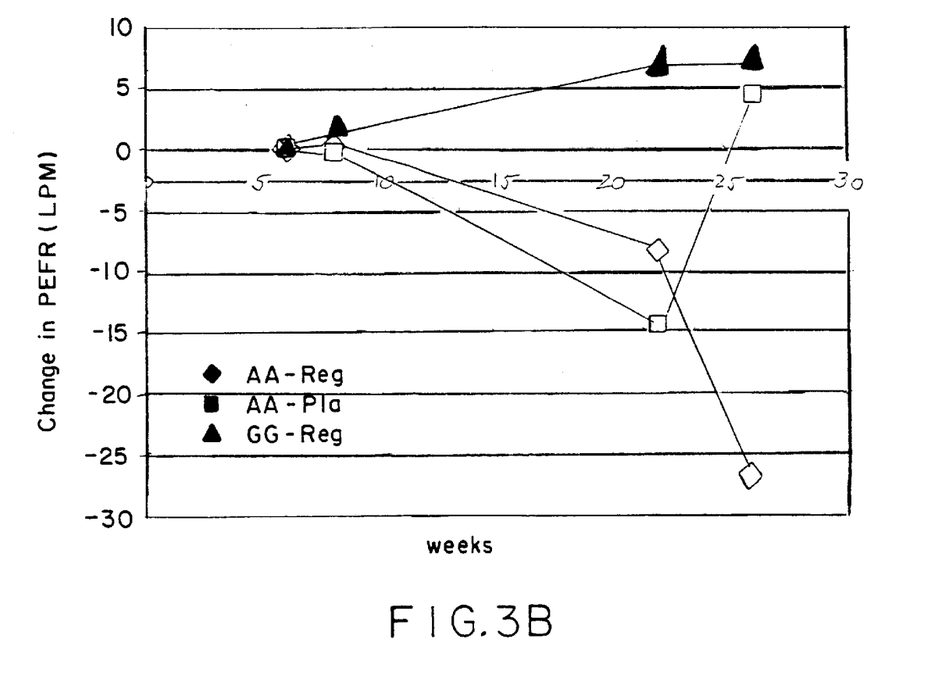

FIG. 3 presents an example of the results we achieved in our genotype analysis of BAGS subjects. The overall findings for this residue are at $\beta_2$-adrenergic receptor residue 16 summarized below in Table 4:

TABLE 4

GENOTYPE OF BAGS STUDY PARTICIPANTS AT PROTEIN RESIDUE 16

| RACE | AA | AG | GG | TOTAL |
|---|---|---|---|---|
| African American | 7 | 12 | 11 | 30 |
| Hispanic | 2 | 9 | 3 | 14 |
| Other Minority | 1 | 4 | 4 | 9 |
| Non-Minority | 18 | 64 | 44 | 126 |
| Total | 28 | 89 | 62 | 179 |

These data indicate an allele frequency of 0.405 for Arg 16, so that one would expect approximately 16% of the population to be homozygous for this allele.

Having determined the $\beta$-adrenergic receptor genotype of BAGS participants, we then re-analyzed the BAGS data, stratifying it by the genotype of the individuals in the various treatment groups. Our results are shown in FIG. 3. As can be seen, individuals who are homozygous for the Arg16 had an adverse response to the regular use of inhaled $\beta$-agonists, as indicated by a decrease in peak flow of 22.5 LPM between the end of the placebo "run-in" period and the end of the "withdrawal" period. By contrast, Arg16 homozygotes who received as-needed $\beta$-agonist treatment had a slight increase in peak flow over this interval. Gly16 homozygotes and Arg16/Gly16 heterozygotes treated with regularly-scheduled $\beta$-agonist administrations, did not display any adverse effects. These data indicate that the genotype at position 16 of the $\beta_2$-adrenergic receptor provides strong predictive information about the likely response of the patient to regularly-scheduled $\beta$-agonist treatment. The change in peak flow rate after regularly-scheduled albuterol treatment was significantly different over the interval between the end of the run period and the end of the withdrawal period in individuals homozygous for the Arg16 allele as compared with those having the Gly16/Gly16 or Arg16/Gly16 genotypes (p=0.0019 for AM PEFR; p=0.0009 for PM PEFR).

We note that all of the $\beta$-agonist-sensitive Arg16 homozygotes that we analyzed were also homozygous for Gln27, but other Gln27 homozygotes did not have adverse responses to $\beta$-agonists. Accordingly, we conclude that Gln27 is not likely to be an indicator, by itself, of susceptibility to adverse $\beta$-agonist responses. However, preferred methods of the present invention will assay genotype at both residue 16 and residue 27, and will identify individuals susceptible to adverse $\beta$-agonist reaction as those that are homozygous for both Gln27 and Arg16.

Example 3
Preferred Methods of Detecting β₂-Adrenergic Receptor Alleles

Generally:

As will be readily appreciated by those of ordinary skill in the art, any of a variety of techniques may be used to detect β₂-adrenergic receptor alleles in order to identify patients susceptible to a negative response to β-agonist administration in accordance with the present invention. The present Example is intended only to provide certain preferred examples of possible methods, and is not intended to limit the scope of the present invention.

Temperature Gradient Gel Electrophoresis:

GENERALLY: A temperature gradient gel electrophoresis method for detection of β₂-adrenergic receptor gene polymorphisms has been described (Reihsaus et al., *Am. J. Respir. Cell. Mol. Biol.* 8:334, 1993, incorporated herein by reference). Basically, a gradient of denaturing solvent in a polyacrylamide gel is employed to separate nucleic acid fragments that differ in sequence by only a single base pair (see, for example, Wartell et al., *Nuc. Acids Res.* 18:2699, 1990, incorporated herein by reference).

GEL ELECTROPHORESIS: Temperature-gradient gel electrophoresis can be carried out with a vertical acrylamide slab-gel apparatus, modified from a conventional vertical gel apparatus so that the glass plates containing the acrylamide gel are sandwiched between two aluminum heating blocks. Channels in the blocks allow circulating fluid to establish a temperature gradient from the top to bottom or from one side to the other. The channels running across the top and bottom are used to establish a temperature gradient in the same direction as electrophoretic migration. For a gradient perpendicular to DNA migration the fluid flows along the sides. Adhesive pipe tape is used to insulate the surfaces of the blocks not facing the glass. The rear block is placed against the main vertical support of the gel unit in the space formed by the overhanging upper buffer chamber. Both heating blocks rest on U-shaped plexiglass pieces which keep them above the buffer in the lower electrolyte chamber. Two thermostated fluid circulators (Haake Inc.) are employed to control the high and low temperatures.

The temperature gradient produced by the heating blocks is preferably checked for linearity and uniformity at least two temperature settings of the water circulators (e.g., 32° C./28° C. and 44° C./18° C.). A thermistor probe (±0.5° C.) can be inserted into a gel to determine the gel temperatures at different depths and horizontal positions. For all temperature settings, the gradient in the gel is preferably linear and uniform within the region covered by the blocks. The appropriate percent acrylamide gel is determined according to standard practice. Such gels should be prepared in a denaturing solvent (e.g., 0.5M TBE, 7.0M urea, 40% formamide u/u) gels are loaded and according to standard procedures.

CALCULATION OF THERMAL STABILITY PROPERTIES: The model of the DNA helix-coil transmission can be used to calculate the thermal denaturation behavior of the DNA fragments (see Wartell et al., *Nuc. Acids Res.* 18:2699, 1990, and references cited therein). In addition to predicting the melting curve for a given DNA sequence, the calculation can also produce melting profiles for the base pairs in a DNA sequence. A melting profile displays the probability that the $n^{th}$ base pair of the sequence is melted, θ(n), at a given temperature. From a three dimensional display of melting profiles at a series of temperatures the lengths and locations of cooperatively melting domains can be visualized. The calculation of the melting profiles assumes that strand dissociation is negligible.

The nearest neighbor stacking parameters can be obtained from McCampbell et al. (*Biopolymers* 28:1745, 1989), and Gotoh and Tagashira (*Biopolymers* 20:1033, 1981). All other parameters, such as the loop entropy factor, strand dissociation parameters, etc. can be obtained from McCampbell et al. (*Biopolymers* 28:1745, 1989). When only the first melting domain is of concern the dissociation parameters and loop entropy terms do not significantly influence theory-experiment comparisons. Extrapolations may be required to normalize the calculations to the solvent conditions utilized in the above-cited parameter references. For example, the Gotoh and Tagashira parameters, determined in 0.02M Na⁺, can be extrapolated to 0.1 M Na⁺ by scaling $T_{AT}$ and $T_{GC}$, the average $T_m$'s of AT and GC base pairs (Vologodskii et al., *J. Biomole Struct. Dynam.* 2:131, 1984).

Allele-Specific PCR:

GENERALLY: One preferred method for identifying β₂-adrenergic receptor gene polymorphisms in order to practice the present invention is to perform polymerase chain reactions (PCR) using primers whose 3'-most nucleotide is mismatched with respect to either the Arg 16 allele or the Gly 16 allele (see Newton et al., *Nuc. Acids. Res.* 17:2503, 1989, incorporated herein by reference; see also Example 2). The PCR reaction conditions are then adjusted so that product band is only produced when the primer and template are matched.

Useful PCR primers and conditions for detection of the Arg 16 and Gly 16 β2-adrenergic receptor gene alleles have been described (Turki et al., *J. Clin. Invest.* 95:1635, 1995, incorporated herein by reference; see also Example 2). As described in that article, allele-specific PCR is based on the premise that, under the appropriate conditions, a match between template and primer at the most 3' nucleotide is necessary for the generation of a PCR product (i.e., mismatches result in no product). Allele-specific PCR reactions can be performed, for example, as follows:

Genomic DNA is isolated, for example, from 2 ml of peripheral blood, by any available technique, such as the a cetylmethyl ammonium bromide separation technique (Jones et al., *Nature* 199:280, 1963). PCR reactions are carried out in a vol of 100 μl using~500 ng of genomic DNA. Preferred primer pairs that delineate the two polymorphisms at nucleic acid 46 (amino acid 16), include i) 5'-CTTCTTGCTGGCACCCAATA-3'(sense) (SEQ ID NO:10) and 5'-CCAATTTAGGAGGATGTAAACTTC-3' (antisense) (SEQ ID NO:11); ii) or the same antisense primer and 5'-CTTCTTGCTGGCACCCAATG-3' (sense) (SEQ ID NO: 12). The generated PCR product size using these primers is 913 bp. The polymerase Vent exo (−) (New England Biolabs, Inc., Beverly, Mass.) can be used for these reactions. Reaction buffers are preferably those included with these polymerases from the manufacturers. Temperature cycling is preferably 98° C. for 30 s, 66–68° C. for 45 s, and 72° C. for 45 s for 30 cycles, 20 μl of the PCR reactions can be electrophoresed on 1% agarose gels and visualized with ethidium bromide staining and ultraviolet illumination.

The allele-specific PCR technique can be verified by direct dideoxy sequencing of PCR products, preferably using sequencing primers different from those used in the PCR. In addition, plasmids consisting of wildtype β₂AR cDNA or mutated cDNA corresponding to the polymorphisms can be used as positive and negative control templates for the allele-specific PCR studies.

Hybridization Studies:

GENERALLY: It has long been appreciated that differences in nucleotide sequence can usually be detected by oligonucleotide hybridization under appropriate conditions. Recently, Hall et al. (*Lancet* 345:1213, 1995, incorporated herein by reference) have demonstrated that such techniques may reliably be used to detect sequence differences in the $\beta_2$-adrenergic receptor gene. As they teach, samples of genomic DNA containing the $\beta_2$-adrenergic receptor gene may be immobilized on a filter such as, for example, a Hybond® filter. In preferred methods, the relevant portion of the $\beta_2$-adrenergic receptor gene (i.e., a portion that includes nucleotide 46, encoding residue 16, is amplified by PCR, and the PCR product is affixed to the filter. The filter is then hybridized with excess unlabeled primer (to "block" non-specific reactions). Subsequently, the filter is exposed to labeled primer under high-stringency conditions. The primer is designed to hybridized with either the Gly16 or the Arg16 allele, but not with both under the hybridization conditions employed. In preferred embodiments, the filter is subsequently stripped and re-hybridized (or a duplicate filter is prepared and reacted in parallel) with a primer that reacts with the other allele.

Restriction Fragment Length Polymorphism:

The RFLP technique has long been a popular method for identifying sequence differences within a population (see, for example, Unit 2.7 of *Current Protocols in Human Genetics*, John Wiley & Sons, incorporated herein by reference). The $\beta_2$-adrenergic receptor gene contains a $\beta$an/ site at position 523 (corresponding to amino acid 175 in the protein) that is polymorphic (see Ohe et al., *Thorax* 50:353, 1995). Although this polymorphism has not been shown to demonstrate linkage with the Arg16→Gly polymorphism, standard techniques could readily be employed to detect such a linkage if it exists, so that utilized in the practice of the present invention.

Protein Assays

The presence of $\beta_2$-adrenergic receptor polymorphisms can also be detected through protein assays that can distinguish the Arg16 and Gly16 versions of the $\beta_2$-adrenergic receptor protein. For example, Western blots could be performed using monoclonal antibodies specific for either variant. Western blot technologies are well known in the art.

Example 4
Kits for Identification of Individuals Susceptible to Adverse Responses to Chronic $\beta$-Agonist Therapy As will be apparent to those of ordinary skill in the art, reagents useful in the practice of the present inventive methods can usefully be collected together in kits. For example, primer sets for allele-specific polymerase chain reaction studies can be provided together in a single container.

As described above in Example 3, $\beta_2$-adrenergic receptor gene alleles can be distinguished from one another through use of primers whose 3'-most nucleotides hybridize with one allele but are mismatched with respect to others. Examples 2 and 3 describe particular useful primer sets, but those of ordinary skill in the art will readily recognize that variations in precise primer sequence can be made without departing from the spirit or scope of the present invention, so long as one primer set produces an amplification product from one $\beta_2$-adrenergic receptor gene allele (e.g., the allele encoding the Arg16 variant), and a different primer set produces an amplification product from another allele (e.g., the allele encoding the Gly16 variant). Preferred allele-specific PCR kits also include other PCR reagents, such as buffer, salt solutions, dNTPs, control DNA including the Arg16 $\beta_2$-adrenergic receptor gene allele, control DNA including the Gly16 $\beta_2$-adrenergic receptor gene allele, and/or DNA polymerase. Preferably, the DNA polymerase is thermal-stable. Such kits may optionally include instructions for use.

Those of ordinary skill in the art will appreciate that analogous primer-containing kits may be prepared for ligation amplification reactions, which are based on the premise that adjacently-hybridized primers are only ligated together when their terminal residues are hybridized (see English et al., *Proc. Natl. Acad. Sci. USA* 9:630, 1994, incorporated herein by reference). Additional reagents optionally included in ligantion amplification kits include buffers, salts, ligase (preferably thermal-stable ligase), ATP, control DNA including the Arg16 $\beta_2$-adrenergic receptor gene allele, control DNA including the Gly16 $\beta_2$-adrenergic receptor gene allele, and/or instructions for use.

Primer-containing kits may also be desirably prepared that do not contain allele-specific primer sets, but rather contain only a single set of primers, which primers amplify a region of the $\beta_2$-adrenergic receptor gene that encodes residue 16. Preferred such kits also include PCR reagents and/or sequencing reagents. Preferably, dideoxy sequencing reagents are employed (see Sambrook et al., *Molecular Cloning: A Laboratory Manual*, Cold Spring Harbor Laboratory Press, Cold Spring Harbor, N.Y., 1989, Chapter 13, incorporated herein by reference). Preferred dideoxy sequencing reagents include, for example, a sequencing primer (that hybridizes either to the $\beta_2$-adrenergic receptor gene amplification product or to a vector into which the product may be cloned), dNTPs, ddNTPs, buffers, salts, and/or instructions. In preferred embodiments, the dNTPs are provided either singly or in mixtures that are sets of three dNTPs. Preferred kits may also (or alternatively) include detection reagents, such as, for example, radioactive or fluorescent. Particularly preferred kits are designed genetic analyzers and include fluorescently-tagged primers.

Some preferred kits also contain reagents for distinguishing other $\beta_2$-adrenergic receptor gene alleles (e.g., alleles at other positions).

Other Embodiments

One of ordinary skill in the art will readily recognize that the foregoing has been merely a detailed description of certain preferred embodiments of the present invention. Various alterations and modifications of the procedures, techniques, and compositions described above will be apparent to those in the art and are intended to be encompassed by the following claims.

We claim:

1. A method of identifying individuals susceptible to adverse responses to regular β-agonist administration, the method comprising steps of:
   i) providing a genomic nucleic acid sample from an individual;
   ii) identifying in said sample a first and second allele of the individuals $\beta_2$-adrenergic receptor gene; and
   iii) classifying the individual as susceptible to adverse responses to regular β-agonist administration if the first and second alleles of the $\beta_2$-adrenergic receptor gene both encode Arg at residue 16 of the $\beta_2$-adrenergic receptor protein.

2. The method of claim 1 wherein the step of identifying employs a technique selected from the group consisting of: denaturing gel electrophoresis, allele-specific polymerase chain reaction amplification, single strand conformation polymorphism analysis, restriction fragment length polymorphism analysis, and allele-specific hybridization.

3. The method of claim 1, wherein the step of identifying comprises amplifying a first portion of the first $\beta_2$-adrenergic receptor gene allele, and a second portion of the second $\beta_2$-adrenergic receptor gene, which first and second portions each include a sequence encoding residue 16 of the $\beta_2$-adrenergic receptor protein.

4. The method of claim 3, wherein the step of identifying further comprises determining the nucleotide sequences of said portions.

5. The method of claim 4 wherein the step of determining constitutes automated sequence analysis.

6. The method of claim 3, wherein the step of identifying comprises amplifying said first portion through use of a primer set that amplifies a sequence encoding Arg at residue 16 of the $\beta_2$-adrenergic receptor protein but does not amplify a sequence encoding Gly at residue 16.

7. The method of claim 3, wherein the step of identifying comprises amplifying said first portion through use of a primer set that amplifies a sequence encoding Gly at residue 16 of the $\beta_2$-adrenergic receptor protein but does not amplify a sequence encoding Arg at residue 16.

8. The method of claim 6, wherein the primer set comprises a first primer having a nucleotide sequence including SEQ ID NO:3 and a second primer having a nucleotide sequence including SEQ ID NO:5.

9. The method of claim 7, wherein the primer set comprises a first primer having a nucleotide sequence including SEQ ID NO:4 and a second primer having a nucleotide sequence including SEQ ID NO:5.

10. The method of claim 1, wherein the step of classifying further includes classifying the individual as susceptible to an adverse response to regular β-agonist administration if the first and second alleles of the β-adrenergic receptor gene both encode Arg at residue 16 and Gln at residue 27 of the β-adrenergic receptor protein.

* * * * *